(12) United States Patent　　(10) Patent No.:　　US 7,985,202 B2
Li et al.　　(45) Date of Patent:　　Jul. 26, 2011

(54) INFUSION DEVICE FOR INFUSING MULTIPLE MEDICAMENTS AT DIFFERENT SPEEDS

(75) Inventors: Nan Li, Shanghai (CN); Shuqun Cheng, Shanghai (CN); Hao Li, Shanghai (CN)

(73) Assignee: Nan Li, Shanghai (CN)

( * ) Notice: Subject to any disclaimer, the term of this patent is extended or adjusted under 35 U.S.C. 154(b) by 0 days.

(21) Appl. No.: 12/901,796

(22) Filed: Oct. 11, 2010

(65) Prior Publication Data

US 2011/0028900 A1　　Feb. 3, 2011

Related U.S. Application Data

(63) Continuation-in-part of application No. 12/125,321, filed on May 22, 2008, now abandoned.

(51) Int. Cl.
*A61M 1/00* (2006.01)
(52) U.S. Cl. ...................................... 604/151
(58) Field of Classification Search .................. 604/151, 604/153, 509, 518, 97.02, 175, 93.01, 891.1, 604/288.01, 288.02, 288.03, 288.04, 890.1, 604/103.01, 103.02, 103.03; 606/191, 192, 606/193, 194
See application file for complete search history.

(56) References Cited

U.S. PATENT DOCUMENTS

| | | | |
|---|---|---|---|
| 4,392,853 | A | 7/1983 | Muto |
| 4,929,236 | A | 5/1990 | Sampson |
| 5,147,323 | A | 9/1992 | Haber et al. |
| 5,286,258 | A | 2/1994 | Haber et al. |
| 6,033,401 | A | 3/2000 | Edwards et al. |
| 6,074,366 | A | 6/2000 | Rogers et al. |
| 6,565,599 | B1 | 5/2003 | Hong et al. |
| 2006/0064053 | A1 | 3/2006 | Bollish et al. |
| 2006/0106361 | A1 | 5/2006 | Muni et al. |

FOREIGN PATENT DOCUMENTS

| | | |
|---|---|---|
| CN | 2201954 | 6/1995 |
| WO | 9820921 | 5/1998 |
| WO | 02074381 | 9/2002 |

*Primary Examiner* — Nicholas D Lucchesi
*Assistant Examiner* — Brooke M Matney
(74) *Attorney, Agent, or Firm* — Kirton & McConkie; Evan R. Witt

(57) ABSTRACT

An infusion device includes a pump forming front and rear chambers for receiving medicaments therein. The medicaments supplied from the two chambers are respectively transmitted into an elastic reservoir forming first and second lumens through first and second passageways. Then, the medicaments are infused into a person through a catheter which defines one passageway toward the human body. The first passageway is in fluid communication with the front chamber and second lumen. The second passageway is in fluid communication with the rear chamber, the first lumen, and the second lumen. By making the diameter of a second hole which connects the first lumen and second lumen smaller than a first hole which connects the first passageway and the first lumen, the medicament from the second chamber can be infused into patient with a low concentration.

16 Claims, 10 Drawing Sheets

INFUSION DEVICE FOR INFUSING MULTIPLE MEDICAMENTS AT DIFFERENT SPEEDS

CROSS-REFERENCES TO RELATED APPLICATIONS

The present application is a continuation-in-part of U.S. patent application Ser. No. 12/125,321, entitled "INFUSION DEVICE FOR INFUSING MULTIPLE MEDICAMENTS AT DIFFERENT SPEEDS AND METHOD", filed on May 22, 2008.

TECHNICAL FIELD OF THE INVENTION

The present invention relates to an infusion device for medical use, and particularly, to an infusion device for infusing multiple medicaments at different rates.

BACKGROUND OF THE INVENTION

Conventionally, medicament infusion pumps are embedded subcutaneously and are widely used to provide medicaments continuously for a period of time, in chemotherapy or for relieving pain of patients. Medicaments which are provided in the afore-said manner would make good curative effects and have insignificant side-effects. Nevertheless, a continuous delivery of low concentration medicaments is often needed to conjunct with high dose medicaments injection in the clinical and medical practices and applications, and a prior-art chemotherapy pump cannot fulfill this purpose.

Consequently, the present invention aims to provide an infusion device, which forms two chambers to meet actual needs for clinical and medical services. The infusion device can be completely embedded in a human body, or alternatively, a pump of the infusion device can be left outside the human body with an injection catheter of the infusion device embedded in the body cavity or blood vessels. The infusion device provided by the present invention is more adaptive for the actual requirements and has improved competition power in the market.

SUMMARY OF THE INVENTION

The present invention provides an infusion device, by which multiple medicaments can be infused at different rates.

In accordance with the present invention, an infusion device comprises: a pump having a front chamber and a rear chamber; a reservoir having a first lumen and a second lumen; a first passageway in fluid communication with the front chamber and the second lumen; a second passageway in fluid communication with the rear chamber, the first lumen, and the second lumen; and a catheter connected to the reservoir. The first lumen and second lumen are separated by a septum with an outlet hole communicating therebetween. The first passageway is in fluid communication with the reservoir through an inlet bore. The diameter of the outlet hole is smaller than that of the inlet bore. The first passageway and second passageway are embodied in a tube. The adjacent parts of the pump, the tube, the reservoir, and the catheter are connected with each other by male joints and female joints. Each male joint is affixed with a seal cartridge.

DETAILED DESCRIPTION OF THE INVENTION

Figure 1:
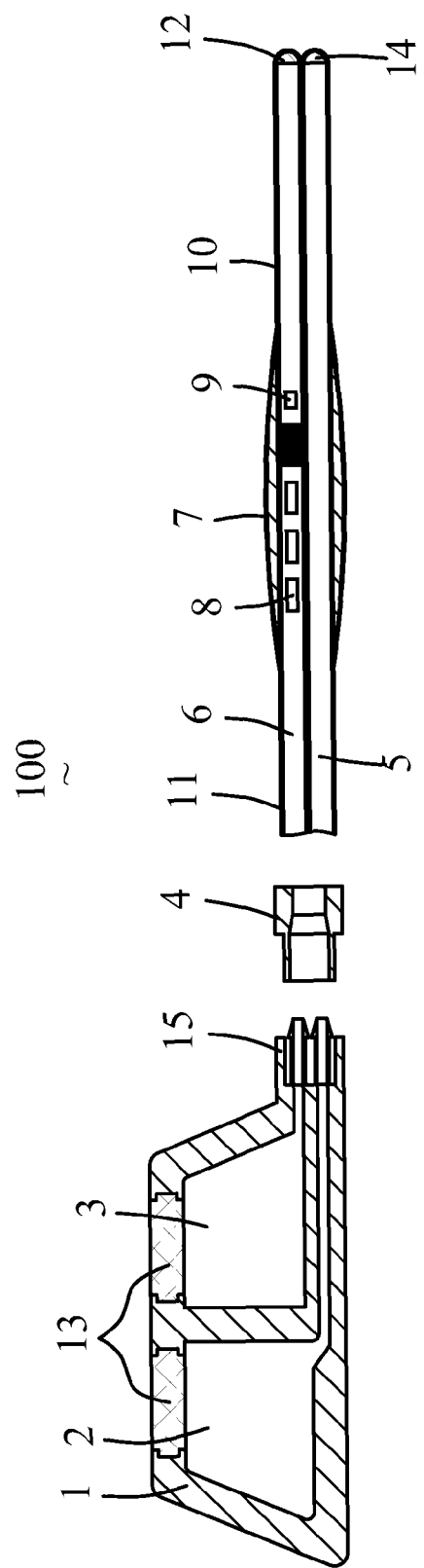
FIG. 1 is a schematic perspective view showing an infusion device of U.S. Ser. No. 12/125,321.

Details of the present invention will be described as follows.

For solving the problem of known prior art chemotherapy pumps being incapable of effecting injection of high dose medicaments while continuously delivering low concentration medicaments, the afore filed application U.S. Ser. No. 12/125,321 provides an infusion device for selectively infusing various medicaments at different rates. The infusion device is not only capable of attaining the curative amount rapidly through one time injection of higher dose medicaments, but also capable of keeping the consistency of continuously infused medicament at a constant value. Thus, the infusion device enhances the curative effects and also simplifies the operation. Accordingly, the inconvenience of long infusion time can be avoided, and the patients' quality of life can be effectively enhanced.

In one aspect, the afore filed application provides a method of infusing multiple medicaments at different rates and being also capable of injecting high dose medicaments and continuously delivering low concentration medicaments by using an infusion device. The infusion device comprises a pump having a first chamber, a second chamber, an outlet tube, and a top surface having a penetrable membrane covering the first chamber and second chamber; an injection catheter having an inlet port, an outlet port, a first passageway which is connected to the first chamber, and a second passageway; and a high-resilient elastic pouch which is mounted to the injection catheter and connected to the second chamber through a plurality of inlet holes defined in a wall of the second passageway, and also connected to the outlet port through a plurality of outlet holes defined in the wall.

In another aspect, the afore filed application provides an infusion device for infusing multiple medicaments at different rates; the infusion device at least comprises: a pump having a first chamber, a second chamber, an outlet tube, and a top surface having a penetrable membrane covering the first chamber and second chamber; an injection catheter including an inlet port, an outlet port, a first passageway which is connected to the first chamber, and a second passageway; a high-resilient elastic pouch mounted to the injection catheter connected to the second chamber through a plurality of inlet holes defined in a wall of the second passageway and connected to the outlet port of the injection catheter through a plurality of outlet holes also defined in the wall of the second passageway.

In yet another aspect, the afore filed application provides an infusion device for infusing multiple medicaments at different rates; the infusion device at least comprises: a pump having a plurality of chambers, an outlet tube, and a top surface having a penetrable membrane covering the chambers; an injection catheter having an inlet port, an outlet port, and a plurality of passageways, wherein at least one passageway is connected to one of the chambers; and a plurality of high-resilient elastic pouches mounted to the injection catheter and each connecting to a respective one of the chambers through a plurality of inlet holes defined in a wall of the second passageway and connecting to the outlet port of the injection catheter through a plurality of outlet holes also defined in the wall.

A perspective view of the infusion device of the afore filed application U.S. patent application Ser. No. 12/125,321 is shown in FIG. 1. The infusion device 100 comprises a pump 1 with a first chamber 2 and a second chamber 3 therein. An injection catheter 10 outputs the medicaments in the pump 1. Specifically, a first passageway 5 accommodated in the catheter 10 outputs the first medicament in the first chamber 2, and a second passageway 6 accommodated in the catheter 10 outputs the second medicament in the second chamber 3. A high-resilient elastic pouch 7 mounted to an outer surface of the injection catheter 10 is fluid contact with the second passageway 6 through a plurality of inlet holes 8. The high-resilient elastic pouch 7 is further fluid contact with the outlet port 14 of the catheter 10 through a plurality of outlet holes 9. The inlet holes 8 and outlet holes 9 are all defined in the wall of the second passageway 6. The number of the inlet holes 8 of the second passageway 6 is greater than that of the outlet holes 9.

More specifically describing the invention, the aforementioned modes can be realized by the following steps:

First, a pump that is made from hard plastics constitutes an infusion device having two or more chambers according to the present invention, and then, a coating of aliphatic polycarbonate polyurethanes is set on the outer surface of the pump. The pump is shaped as two-connected circles and having a flat bottom and a smooth outer perimeter, also having a long axis of, for example, 4.0 cm, a short axis of, for example, 2.4 cm, and a height of, for example, 1.2 cm. Further, a penetrable membrane is set on the pump to seal the chambers. The penetrable membrane has a long axis of, for example, 3.0 cm and a short axis of, for example, 1.8 cm. The chambers include a front chamber and a rear chamber, where the front chamber is connected to an upper passageway of an injection catheter of the infusion device, and the rear chamber is connected to a lower passageway of the injection catheter through a high-resilient elastic pouch.

The shapes of the pump 10 and the elastic reservoir 20 can be of different shapes according to the size that is appropriate for the patients to taking portably or for other curative services.

Figure 2:
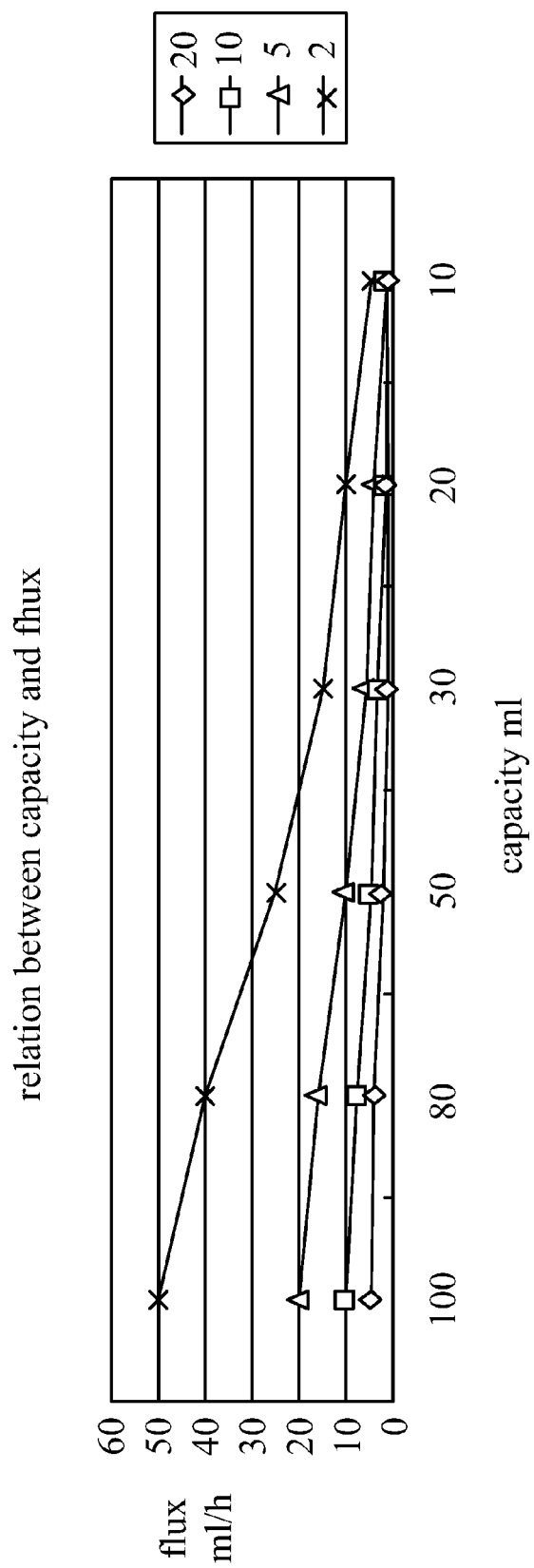
FIG. 2 shows the relationship between volume and flow rate of the infusion device according to the present invention.

The high-resilient elastic pouch of the infusion device can be made of, for example, medical grade silicone rubber. The elastic pouch is covered with a coating of aliphatic polycarbonate polyurethanes and is connected to the front chamber of the pump through a plurality of holes defined in a wall of the upper passageway of the injection catheter. The size of the high-resilient elastic pouch is selectively set according to the therapeutic requirement of treatments. And the volume of the elastic pouch can be set to be 100 ml to 200 ml, for example. The relationship between volume and flow rate according to the present invention is shown in FIG. 2.

Additionally, the part of the injection catheter between inlet holes and outlet holes of the elastic pouch is blocked so that medicament flowing through the upper passageway is only allowed to transmit through the inlet holes, the elastic pouch, and the outlet holes, in sequence. According to the needed infusion speed, the diameter of the outlet holes can be measured by the following equation:

$$\pi(\text{diameter of hole}/2)^2 = (\text{volume of the elastic pouch})/(\text{infusion speed} * \text{delivery time})$$

As far as the injection catheter is concerned, the length of the injection catheter can be 35 cm, for example. A front end of the injection catheter is connected to a tube of the pump by a connector, and a rear end is mounted with an anti-backflow device which can be an elastic crack tip or a check valve, for example.

If the pump of the infusion device is positioned outside the human body, the injection catheter can be fixed on a puncture site by a clamp. If the pump and the elastic pouch are positioned beneath the skin, the shape of the infusion device can be different designs in accordance with the patients' sizes for portable convenience.

The medicament delivery infusion device of U.S. Ser. No. 12/125,321 is capable of not only injecting higher dose medicaments, but also delivering lower concentration medicaments continuously. The coating of the aliphatic polycarbonate polyurethanes on the outer surface of the infusion device is biocompatible and elastic, by which the occurrences of the rejection reactions can be avoided. The anti-backflow device can effectively prevent the injection catheter from being blocked due to a reverse flow, so as to ensure that the medicaments are delivered smoothly in the passageways. However, as referred in the above descriptions, the first and second medicaments in the pump are needed to be transmitted into abdominal cavity by two passageways, respectively by the first passageway and the second passageway. Such a system is difficult and expensive to manufacture.

Figure 3:
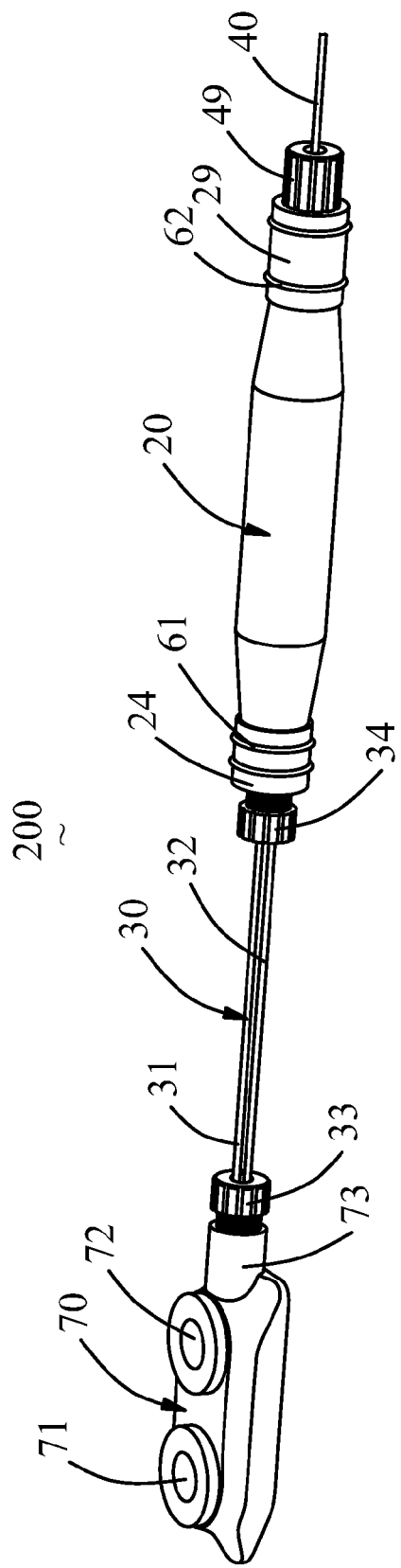
FIG. 3 is a perspective view showing an infusion device according to the present invention.
Figure 4A:
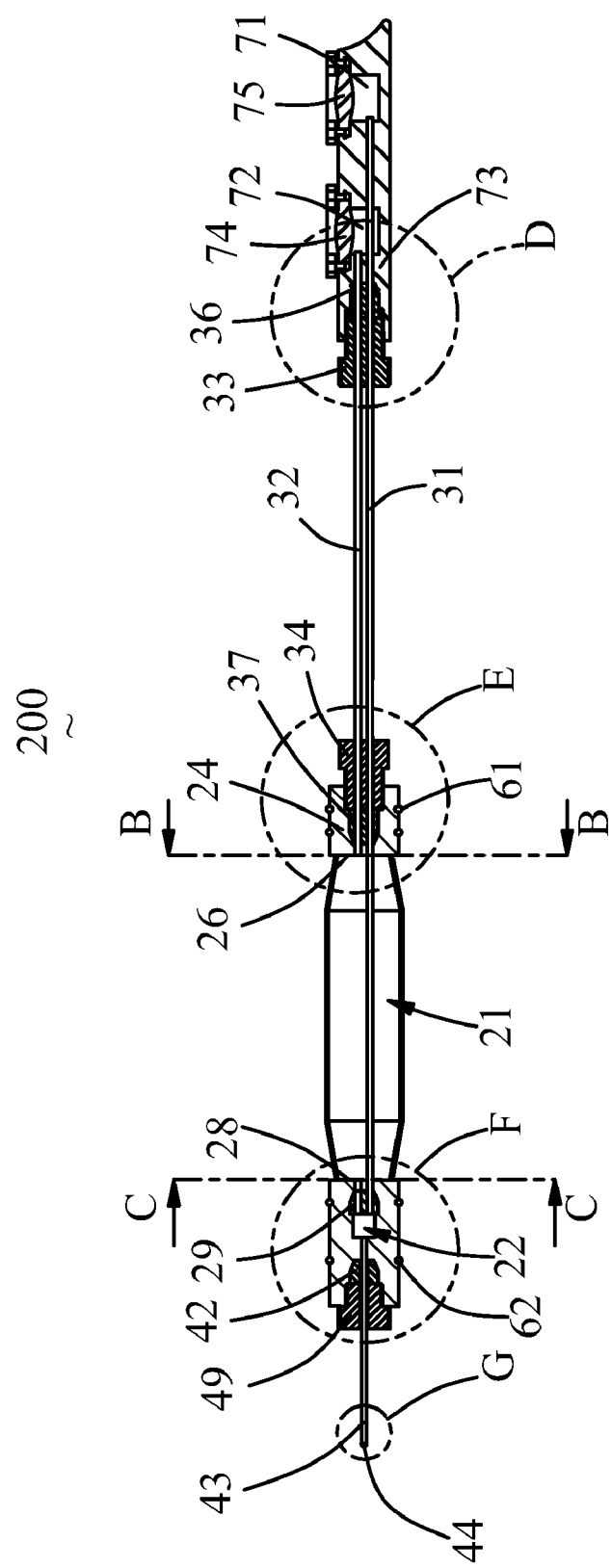
FIG. 4A is a cross-sectional view of the infusion device shown in FIG. 3.
Figure 4B:
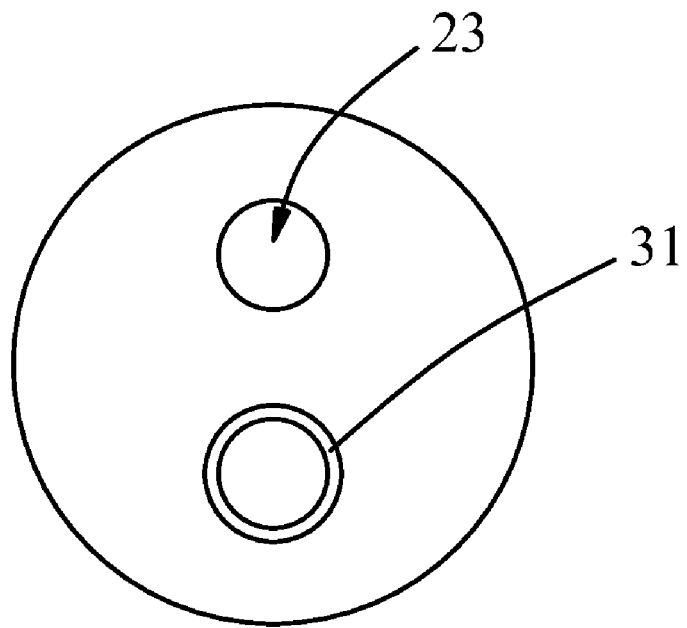
FIG. 4B is a cross-sectional view of the infusion device taken along line B-B of FIG. 4A.
Figure 4C:
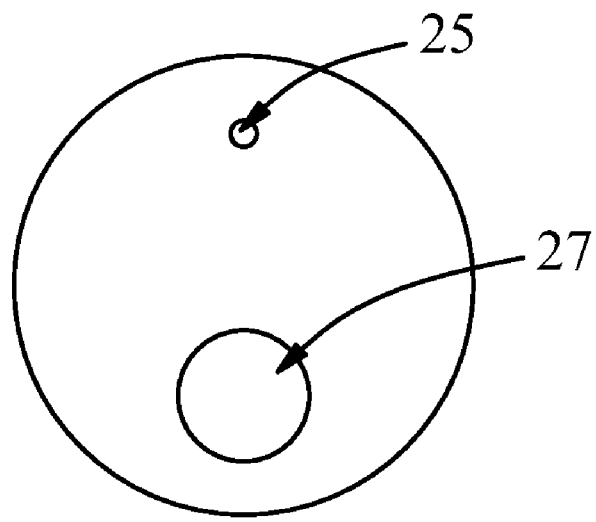
FIG. 4C is a cross-sectional view of the infusion device taken along line C-C of FIG. 4A.
Figure 4D:
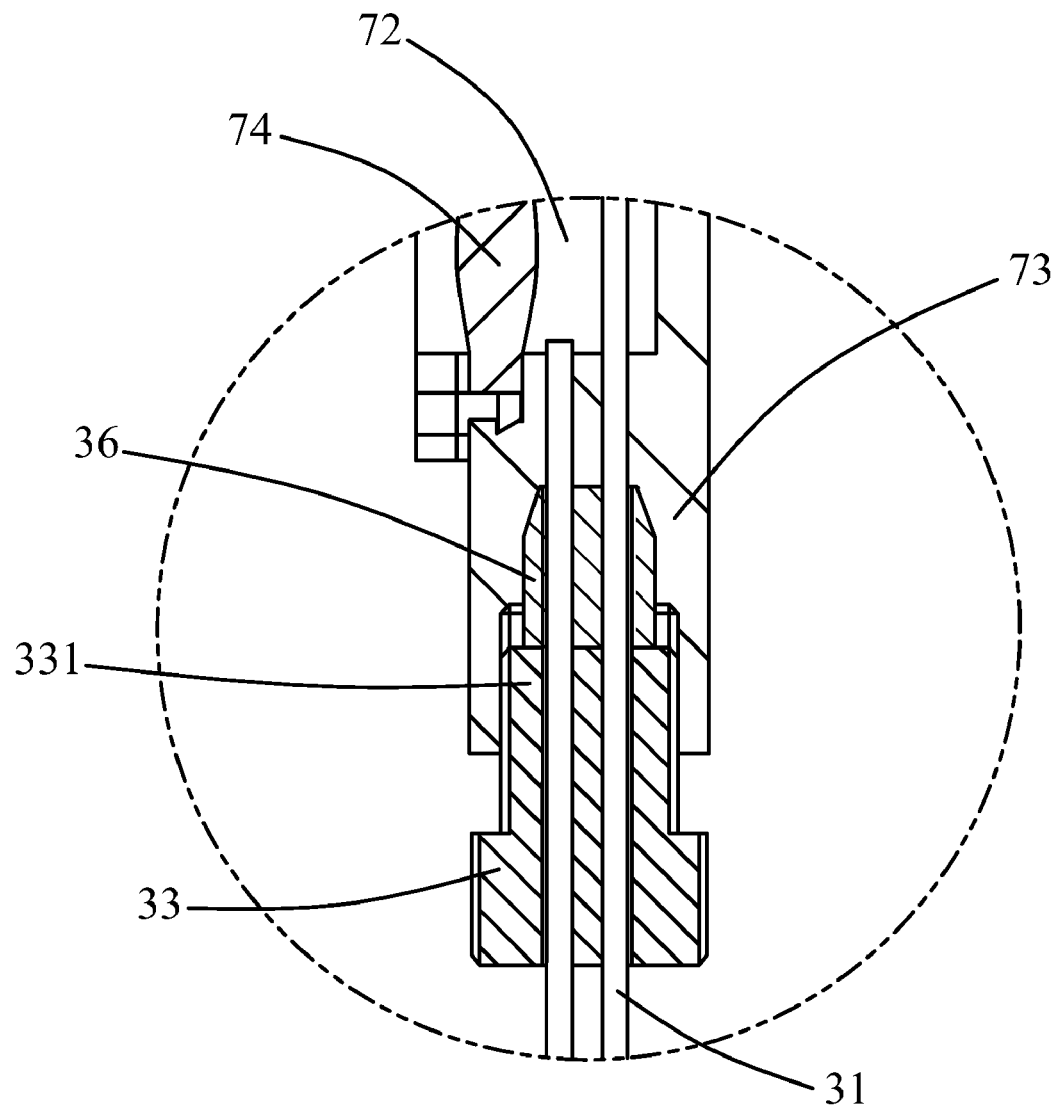
FIG. 4D is an enlarged view of the part D shown in FIG. 4A.
Figure 4E:
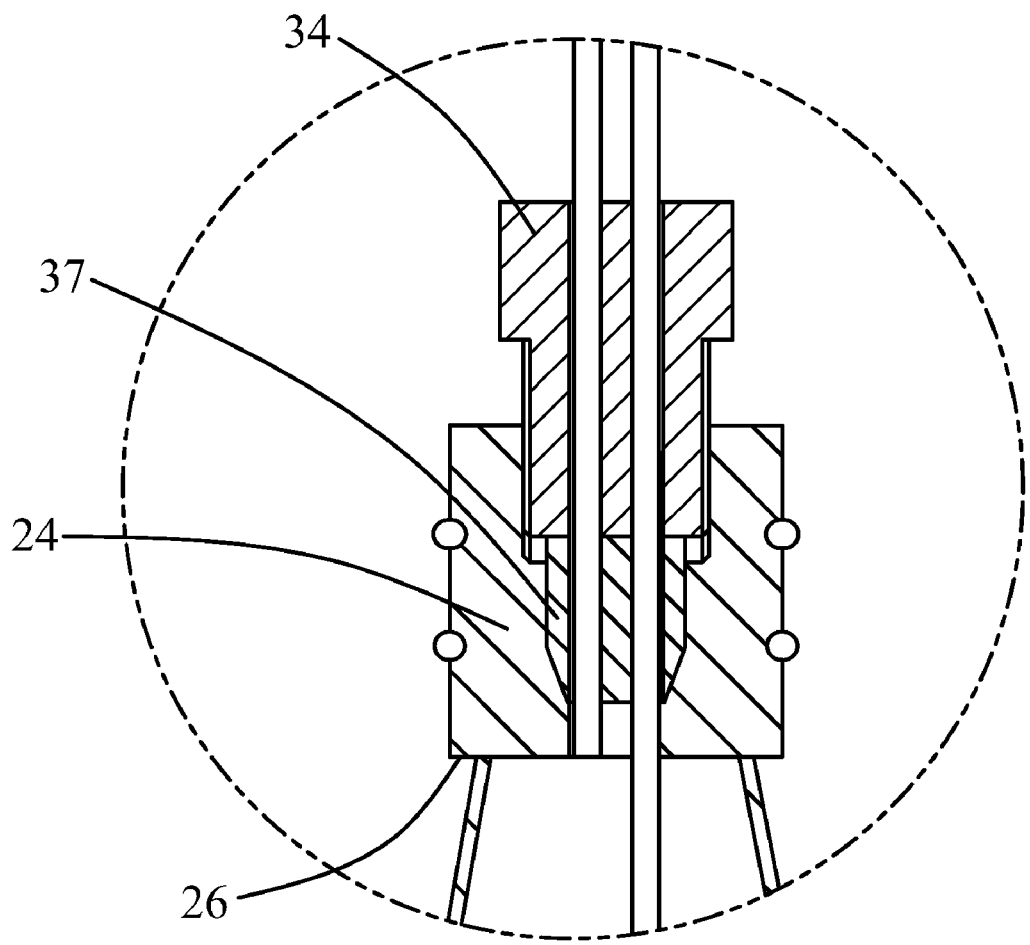
FIG. 4E is an enlarged view of the part E shown in FIG. 4A.
Figure 4F:
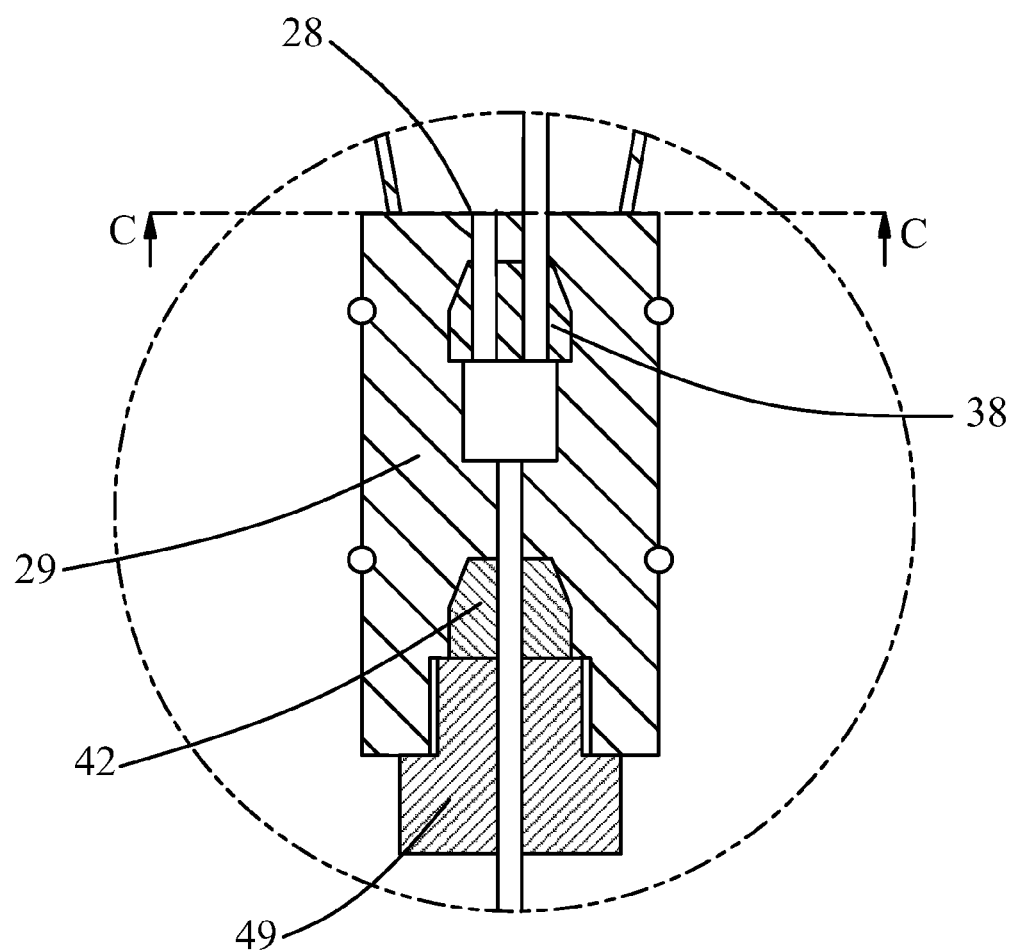
FIG. 4F is an enlarged view of the part F shown in FIG. 4A.
Figure 4G:
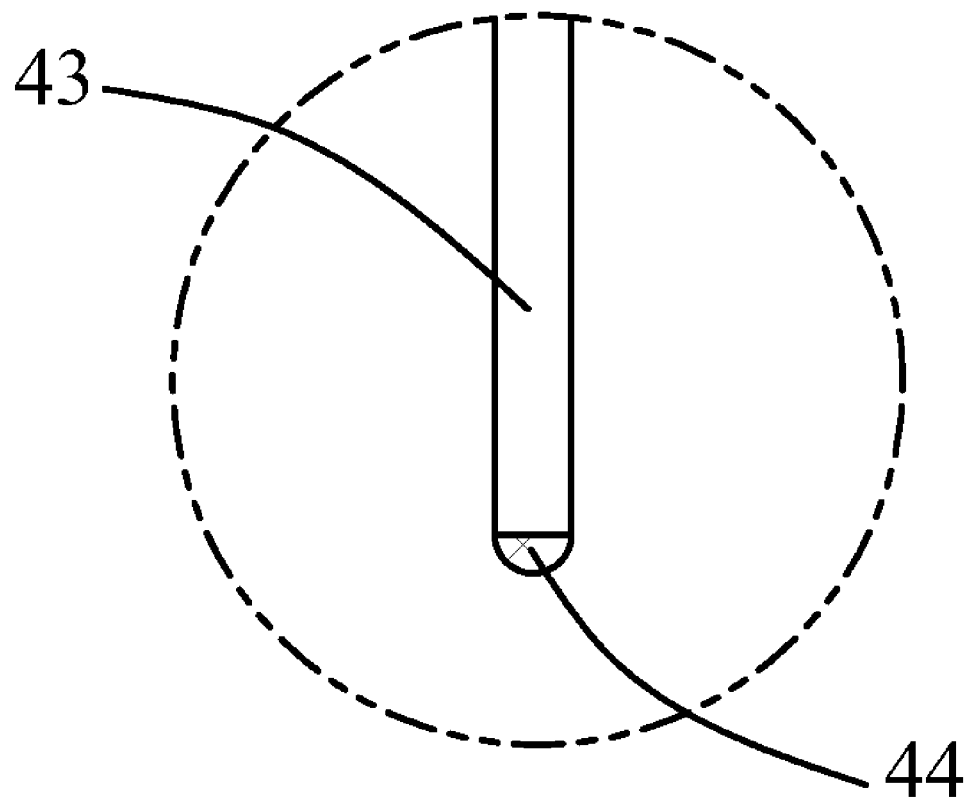
FIG. 4G is an enlarged view of the part G shown in FIG. 4A.
Figure 5:
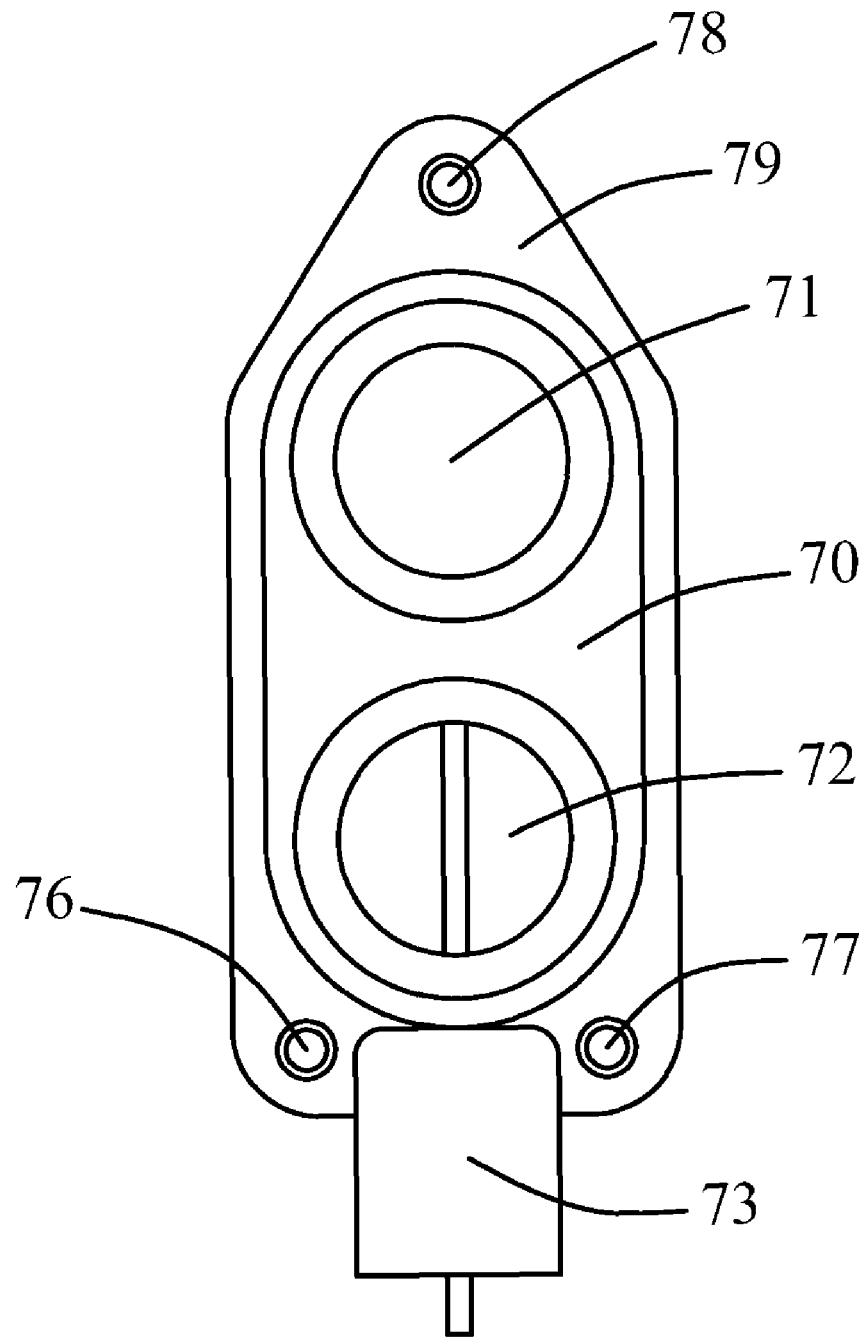
FIG. 5 is a top view of a pump constructing in part the infusion device shown in FIG. 3.

Referring now to FIGS. 3-5, an infusion device 200 according to a preferred embodiment of the present invention, which is constructed as a modification of the device disclosed in afore filed U.S. Ser. No. 12/125,321, is depicted. FIG. 3 is a perspective view illustrating the infusion device according to the preferred embodiment of this application. FIG. 4A is a cross-sectional view of the infusion device shown in FIG. 2. FIG. 4B is a cross-sectional view of the infusion device of the present invention taken along line lane B-B of FIG. 4A. FIG. 4C is a cross-sectional view of the infusion device of the present invention taken along line C-C of FIG. 4A. FIG. 4D is an enlarged view of the part D shown in FIG. 4A. FIG. 4E is an enlarged view of the part E shown in FIG. 4A. FIG. 4F is an enlarged view of the part F shown in FIG. 4A. FIG. 4G is an enlarged view of the part G shown in FIG. 4A. FIG. 5 is a top view of a pump, which is designated at 70 and constructs in part the infusion device shown in FIG. 3.

As illustrated in FIGS. 3 and 4A, the infusion device 200 according to the preferred embodiment of the present applicant comprises a pump 70 and an elastic reservoir 20. The pump 70 forms at least a front chamber 71 and a rear chamber 12 lying behind one another in a direction of fluid flow. The front chamber 71 receives a first medicament therein and the rear chamber 12 receives a second medicament therein. The first and second medicaments can be different and are transmitted respectively into the reservoir 20 through a first passageway 31 and a second passageway 32. Thereafter, the medicaments are delivered into the abdominal cavity by a common catheter 40, which defines a passageway for delivering the medicaments to the human body.

The arrangement of the front chamber 71 and rear chamber 12 to be lined up in the direction of fluid flow and thus located behind one another is to make a distinction between the two chambers, so that a certain chamber may be individually taken and used as desired in different situations.

Referring now to FIGS. 4A and 4D-4F, the first passageway 31 extends from the first chamber 71 to a lumen 22 and the second passageway 32 extends to another lumen 21, both lumens being formed inside the reservoir 20. To simplify the description, the lumens 21, 22 will be referred to as "first lumen" and "second lumen" respectively. A first septum 26 and a third septum 28 are incorporated in the reservoir 20 to divide an interior space of the reservoir 20 into the first lumen 21 and the second lumen 22. The second lumen 22 is provided for receiving all the medicaments, namely both the first and second medicaments. The second lumen 22 is directly connected to the catheter 40. Through the second lumen 22, all the medicaments, including both the first and second medicaments, supplied from the pump 70 are transmitted into the catheter 40. In other words, the second medicament, which is transmitted through the second passageway 32 and the first lumen 21 and the first medicament, which is transmitted only through the first passageway 31, are both fed to the catheter 40. Further details will be given as follows.

As illustrated in FIGS. 4B and 4C, to make the second medicament be infused in a low concentration, a first hole 23 is formed in the first septum 26 of the reservoir 20 for fluid communication between the second passageway 32 and the first lumen 22, and a second hole 25 is formed in the second septum 28 of the reservoir 20 for fluid communication between the first lumen 21 and the second lumen 22. The diameter of the second hole 25 is made smaller than that of the first hole 23. Thus, the first medicament from the first chamber 71 is transmitted directly into the second lumen 22 by way of only the first passageway 31, while the second medicament is transmitted first into the first lumen 21 through the second passageway 32 and the first hole 23 and then fed into the second lumen 22 through the second hole 25. By making the difference between the first hole 23 and second hole 25, a low concentration of the second medicament can be achieved. For example, the diameter of the first hole 23 may be 1.1 cm and the diameter of the second hole 25 0.2 cm.

In one embodiment, the diameter of the first hole 23 is made equal to the inside diameter of the second passageway 32. The septa 26, 28 can be for example diaphragms made of a material of desired property, such as high density silicon.

Referring again to FIG. 3, the first passageway 31 and second passageway 32 are connected to the reservoir 20 in a removable manner. This removable arrangement is also between the catheter 40 and the reservoir 20. The first passageway 31 and second passageway 32 are fixed to the pump 70 through a first male joint 33, which is received and mates a female joint 73 formed in the pump 70. Similarly, the first passageway 31 and second passageway 32 are attached to the reservoir 20 through a second male joint 34, which is received in and removably mates a female joint 24 formed in the reservoir 20. The catheter 40 is similarly and removably coupled to the reservoir 20 through releasable engagement between a male joint 49, which is coupled to the catheter 40, and a female joint 29, which is formed in the reservoir 20.

The three mated pairs of joints 33 and 73, 34 and 24, 49 and 29 constitute three compactly constructed locking structures. As illustrated in FIG. 3, the male joints 33, 34, 49 are preferably shaped as "bolts" that carry external threads; on the other hand, the female joints 73, 24, 29 may be thus shaped with receiving bores forming internal threads for mating the external threads of the male joints 33, 34, 49. Additionally, a fluted or knurled cap may be formed on each of the male joints 33, 34, 39 in order to allow fingers to grip firmly and handle easily.

A fixture 61 is provided on an outer surface of the second female joint 24 so as to hold the passageways 31, 32 onto the reservoir 20. Similarly, a fixture 62 is provided on an outer surface of the female joint 29 so as to hold the catheter 40 onto the reservoir 20. Preferably, the fixtures 61 and 62 are rings.

For providing a fluid seal between the two passageways 31, 32 and the pump 70, a seal cartridge 36 (also see FIG. 4D) is mounted on an input end 331 of the first male joint 33 and retained inside the female joint 73. Similarly, as illustrated in FIGS. 4A, 4E, and 4F, a seal cartridge 37 and a seal cartridge 42 are respectively mounted to an input end of the second male joint 34 and an input end of the third male joint 49 and are respectively retained inside the female joints 24, 29. In addition, as illustrated in FIG. 4F, another seal cartridge 38 is received inside the female joint 29 and set adjacent to the septum 28. As illustrated, these seal cartridges may be of the same shape and construction. Each seal cartridge may comprise a first portion having a frusto-conical outer surface and a second portion carrying a cylindrical outer surface.

As illustrated in FIG. 4G, to prevent reverse flows of the medicaments and/or body fluids, an anti-backflow device 44 is arranged on an outlet section 43 of the catheter 40, which defines an outlet hole or opening (not labeled). The anti-backflow device 44 may be an elastic crack tip or a check valve, for example.

To adequately anchor the infusion device in place, suture holes 78, 76, 77 are formed in a flange 79 of the pump 70. As illustrated in FIG. 5, the number of the suture holes is three, but can be different if desired. The three holes 78, 76, 77 are set at different orientations with respect to the pump 70. One of the holes (hole 78) is located in an imaginary line extending in the fluid flow direction and substantially bisecting the pump 70, while the other two holes (holes 76, 77) are symmetrically arranged with respect to the line. Preferably, the lines connecting between the three holes form a triangle.

The infusion device according to the present invention is designed to be used in abdominal operation. The outer surface of the infusion device is provided with a coating of aliphatic polycarbonate polyurethanes to make it capable of being embedded in or bio-compatible with a living body. The material of the pump 70 can be for example titanium or polysulfone, and the material of the catheter is silicon of x-ray opaque or purchaser of x-ray opaque.

In operation, the outlet section 43 of the injection catheter 40 is set in a vessel or abdomen. If an injection of a high dose medicament (the first medicament) is needed, the first medicament is introduced into the front chamber 71 through a penetrable membrane 75 (see FIG. 4A) covering and closing the front chamber. Then the first medicament is transmitted through the first passageway 31 to the second lumen 22 from which the first medicament is conducted through the catheter 40 to be infused into the objective body cavity or blood vessels in order to affect therapeutic treatment. If a continuous delivery of a low concentration medicament (the second medicament) is needed, the second medicament is introduced into the second chamber 12 by piercing through a penetrable membrane 74 and transmitted to the first lumen 21 of the elastic reservoir 20 through the first hole 23 of the first septum 26. Then, the second medicament is diffused into the second lumen 22 through the second hole 25 defined in the second septum 28. Finally, the second medicament is infused continuously and slowly into the objective body cavity or blood vessels through the catheter 40.

Similar to what described in U.S. Ser. No. 12/125,321, the volume of the elastic reservoir 20 can be made to be of different sizes according to the desired infusion speed or rate. For example, the elastic reservoir 20 can be of a size between 100 ml and 200 ml. The diameter of the outlet holes can also be measured by the afore-mentioned equation.

Further, at least one of the pump 70 and the reservoir 20 may be positioned subcutaneously or out of the body of a patient on surgery. In this case, the end of the injection catheter 40 can be made to puncture through the skin and be set in the body cavity or the vessel. The portion of the injection catheter 40 exposed outside human body is fixed on the body surface by a clamp (not shown).

While the preferred embodiments of the present invention have been illustrated and described in detail, various modifications and alterations can be made by persons skilled in this art. The embodiment of the present invention is therefore described in an illustrative but not restrictive sense. It is intended that the present invention should not be limited to the particular forms as illustrated, and that all modifications and alterations which maintain the spirit and realm of the present invention are within the scope as defined in the appended claims.

What is claimed is:

1. An infusion device comprising:
   a pump forming at least a front chamber and a rear chamber lined up in a direction of fluid flow;
   an elastic reservoir forming at least a first lumen and a second lumen therein;
   a first passageway in fluid communication with the front chamber and second lumen;
   a second passageway in fluid communication with the rear chamber, the first lumen, and the second lumen; and
   a catheter connected on the reservoir;
   wherein each of the chambers is covered with and closed by a penetrable membrane for respectively receiving first and second medicaments therein;
   the second passageway communicates with the first lumen through a first hole, the first lumen communicating with the second lumen through a second hole, the second hole having a diameter smaller than a diameter of the first hole; and
   the catheter defines a passageway adapted to deliver the medicaments to a human body.

2. The infusion device as claimed in claim 1, wherein the first passageway and second passageway are attached to the pump and the reservoir through two male joints, which are respectively received in mateable female joints defined in the pump and the reservoir.

3. The infusion device as claimed in claim 2, wherein the male joints are constructed to carry external threads thereon engaging internal threads formed in bores defined in the female joints.

4. The infusion device as claimed in claim 2, wherein each of the male joints has an input end to which a seal cartridge is mounted, the seal cartridge being received in the corresponding female joint.

5. The infusion device as claimed in claim 3, where each of the male joints has an input end to which a seal cartridge is mounted, the seal cartridge being received in the corresponding female joint.

6. The infusion device as claimed in claim 1, wherein the pump comprises a flange in which holes are defined for anchoring the pump, the holes being set at different orientations with respect to the pump.

7. The infusion device as claimed in claim 6, wherein the flange of the pump forms three holes for anchoring the pump.

8. The infusion device as claimed in claim 1, wherein the catheter is connected to the reservoir by a male joint, which mates a female joint formed in the reservoir.

9. The infusion device as claimed in claim 1, wherein the catheter comprises an anti-backflow device mounted thereto.

10. The infusion device as claimed in claim 1 further comprising a coating formed on a surface of the infusion device.

11. The infusion device as claimed in claim 10, wherein the coating is made of aliphatic polycarbonate polyurethanes.

12. The infusion device as claimed in claim 1, wherein the first and second holes are respectively defined in two septa, which are made of high density silicon diaphragms.

13. The infusion device as claimed in claim 1, wherein the pump is made of titanium.

14. The infusion device as claimed in claim 1, wherein the pump is made of polysulfone.

15. The infusion device as claimed in claim 1, wherein the catheter is made of silicon of x-ray opaque or purchaser of x-ray opaque.

16. The infusion device as claimed in claim 1, wherein the reservoir is in the form of an elastic pouch.

* * * * *